(12) United States Patent
Pallikaris (10) Patent No.: US 6,589,558 B1
(45) Date of Patent: Jul. 8, 2003

(54) PHOTOABLATABLE LENTICULAR MODULATOR

(76) Inventor: Ioannis G. Pallikaris, Kalessa Gaziou, 71500 Iraklion, Crete (GR)

( * ) Notice: Subject to any disclaimer, the term of this patent is extended or adjusted under 35 U.S.C. 154(b) by 0 days.

(21) Appl. No.: 09/139,368

(22) Filed: Aug. 25, 1998

(30) Foreign Application Priority Data

Sep. 9, 1997 (GR) .......................................... 970100343

(51) Int. Cl.$^7$ ........................... A61K 9/10; A61K 47/36; A61K 47/42
(52) U.S. Cl. ...................... 424/488; 424/484; 514/912; 514/944
(58) Field of Search ........................ 424/486, 484–485, 424/488, 400; 514/912, 944

(56) References Cited

U.S. PATENT DOCUMENTS

| | | |
|---|---|---|
| 4,856,513 A | 8/1989 | Muller |
| 5,277,911 A | 1/1994 | Viegas |
| 5,279,611 A | 1/1994 | McDonnell |
| 5,318,780 A | 6/1994 | Viegas |
| 5,492,135 A | 2/1996 | DeVore et al. |
| 5,587,175 A | 12/1996 | Viegas |

FOREIGN PATENT DOCUMENTS

WO   WO-A-93/04642   3/1993

OTHER PUBLICATIONS

Trokel et al., Dec. 1983, Excimer Laser Surgery of the Cornea, American Journal of Ophthalmology.
Pallikaris et al., 1990, Laser In Situ Keratomileusis, Lasers in Surgery and Medicine.
Gartry et al., Nov./Dec. 1991, Photorefractive Keratectomy With an Argon Fluoride . . . Refractive & Corneal Surgery.

*Primary Examiner*—Edward J. Webman
(74) *Attorney, Agent, or Firm*—McGlew and Tuttle, PC (57) ABSTRACT

Photoablatable modulator for use in Laser ablation processes on the cornea consisting of a mixture of collagen and vegetable gelatins which is formed in situ on the corneal surface to be treated. A small quantity of a solution at a temperature higher of that of the cornea is applied on the corneal surface and is shaped to form an optically centered lenticule by means of a special device. The solution solidifies at corneal temperatures and forms a rigid gel which adheres strongly on the corneal surface. A dye added in the solution enables the visual monitoring of the ablation process. The lenticular modulator produced with the disclosed method is customized to provide an ablation profile that smoothes the corneal surface and additionally removes the geometrical irregularities that may pre-exist on it. The final shape of the cornea corresponds to the shape of the mold used for the preparation of the modulator. The device used for the centering of the modulator on the ocular optical axis may include subsidiary elements that facilitate and verify the correct placement of the lenticule on the corneal surface. Gas flow nozzles for the removal of the ablation by-products may be also built-in the device.

2 Claims, 7 Drawing Sheets

Fig. 3a — central mark, molding surface

Fig. 3b — central mark, molding surface

Fig. 3c — central mark, molding surface

Fig. 3d — central mark, molding surface, transition zone

Fig. 4d reference ring

Fig. 4e reference ring

Fig. 4f reference ring adjustable leg

PHOTOABLATABLE LENTICULAR MODULATOR

Excimer laser ablation of part of the cornea has been used extensively in refractive surgery for the treatment of refractive errors (myopia, hyperopia, astigmatism) of the eye (Photorefractive keratectomy). Moreover excimer laser ablation of the superficial layers of the corneal stroma has been employed to remove subepithelial opacities as well as for the smoothing of the corneal surface (Phototherapeutic Keratectomy).

Generally in photorefractive keratectomy (PRK) or in phototherapeutic keratectomy (PTK) an ArF excimer laser (wavelength 193 nm) is used for the controlled ablation of corneal tissue. Typical operating parameters are: Energy fluence: 100–250 mJ/cm$^2$, repetition rate: 20 pulses/sec, Pulse duration: 20 nsec. The application of Excimer lasers in photoablation procedures of the cornea has been reported extensively in the scientific literature. The following papers can be mentioned as examples:

Trokel S, Srinivasan R, Braren B. Excimer Laser surgery of the cornea, *Am. J. Ophthalmology* 1983; 94:125, Gartry G S, Kerr Muir M G, Marshall J. Photorefractive keratectomy with an argon fluoride excimer laser: a clinical study. J Refractive & Corneal Surgery 1991;7:420–431, Pallikaris I G, Papatzanaki M, Stathi E, Frenschock O, Georgiadis A, Laser in situ keratomileusis. Lasers Surg Med 1990;10:463–468.

The ablation of cornea with the 193 nm excimer laser has excellent precision, and insignificant thermal side effects. In general the tissue beneath the ablation site remains transparent and smooth. The laser irradiation takes place in a series of pulses of predetermined duration, energy and repetition rate which series of pulses is shaped by a series of diaphragms or it is scanned on the corneal surface in order to produce an irradiation pattern capable of changing the shape of the cornea and consequently it's optical performance. The desired dioptric correction determines the total depth of the ablation which is achieved by proper selection of the irradiation parameters (energy, repetition rate total number of pulses) and beam shaping algorithm.

The principal parameter that can modify the refractive outcome in respect to the desired is the change of corneal ablation rate ($\mu$m/pulse) as a result of corneal hydration variations.

In some cases modulators can be used for the creation of the ablation profile. A modulator is a photoablatable element that is placed between the laser source and the corneal surface and during the progress of the ablation process allows the gradual transmission of different portions of the laser beam and finally reproduces an irradiation profile which corresponds to a desired ablation profile.

A polymer modulator which is placed on the optical path of the laser beam delivery system and has the shape of a spherical or toric lens is in wide use for the correction of standard refractive errors (U.S. Pat. No. 4,856,513).

Application of certain collagen solutions on the corneal surface prior to laser irradiation in order to form an in-situ modulator has also been referred (U.S. Pat. No. 5,492,135). This solution while liquid covers the irregularities of the corneal surface while maintaining a relatively smooth anterior surface which is finally "projected" on the corneal surface provided that the collagen gel and the cornea have equal ablation rates.

The case of the remote polymer modulator has the disadvantage of the limited effectiveness in corneas with irregular shapes.

Figure 1:
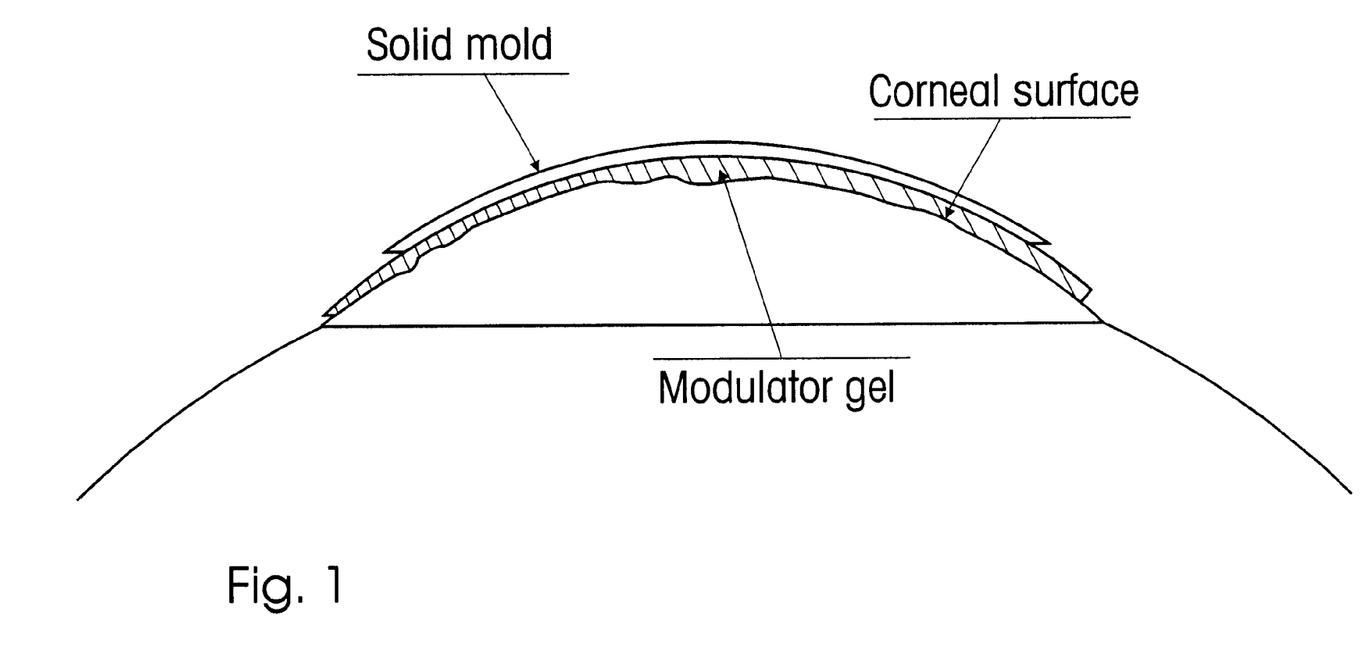
FIG. 1 illustrates a side view of an eye with cornea having irregularities. The posterior surface of the hydrogel modulator follows the corneal irregularities while the anterior is being shaped by a centered thin and lightweight mold.
Figure 2:
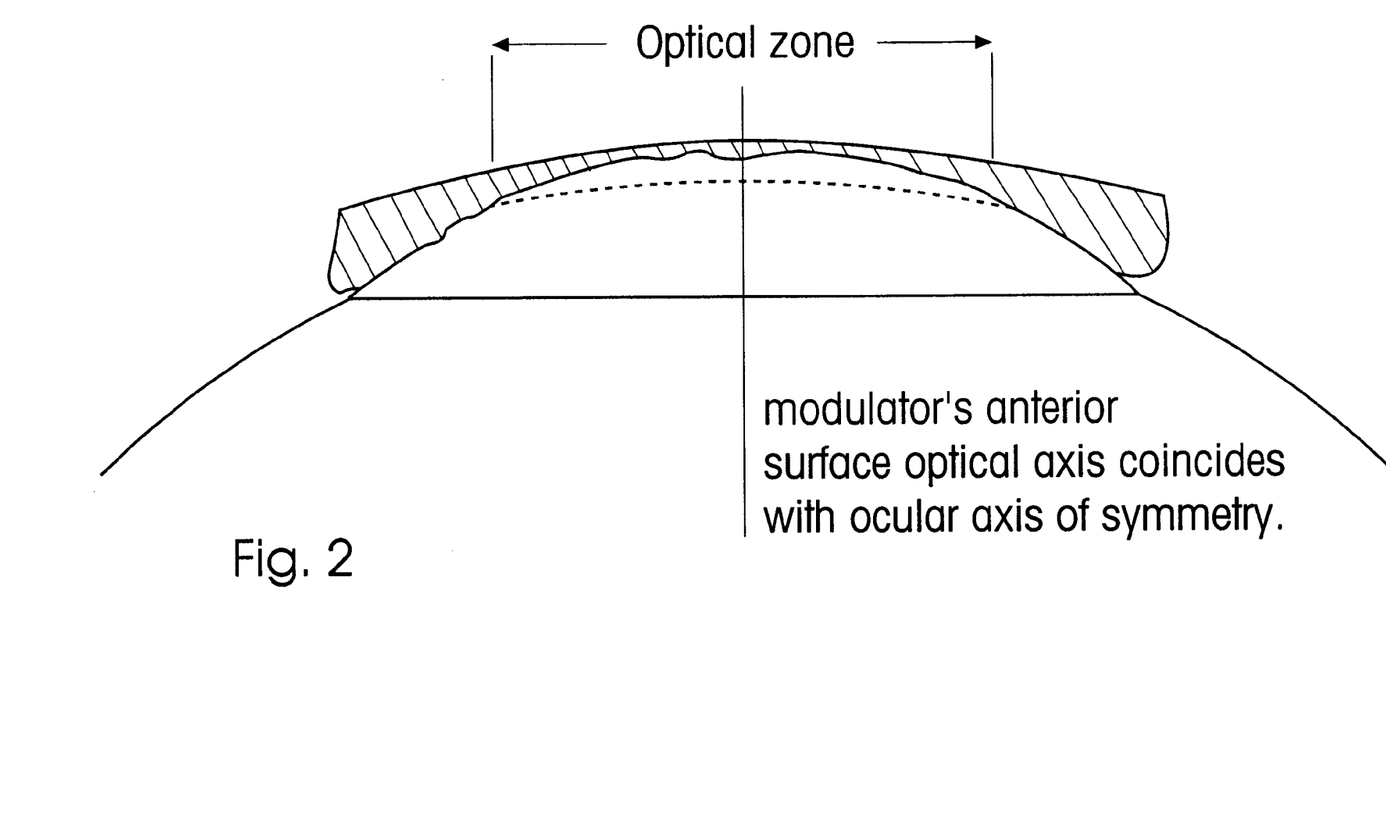
FIG. 2 illustrates a side view of an eye with cornea having irregularities with modulator in place. The effect of such a modulator would be the simultaneous smoothing of the corneal surface and the reduction of it's curvature in order to correct myopia. The dashed line indicates the shape of the cornea after it's partial ablation through the modulator.
Figure 3A:
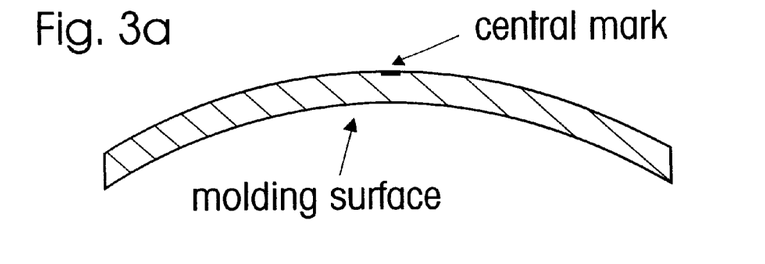
FIGS. 3a–3d illustrate possible configurations of the mold.
Figure 3B:
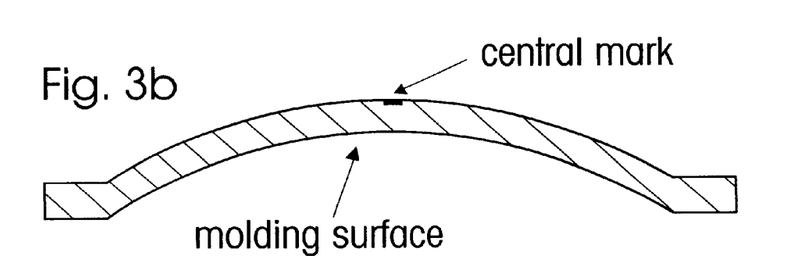
Figure 3C:
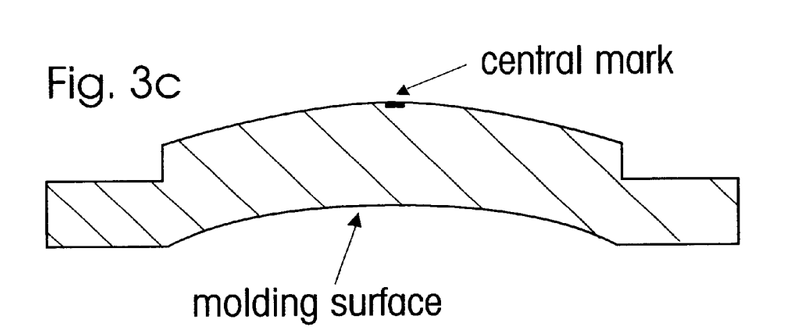
Figure 3D:
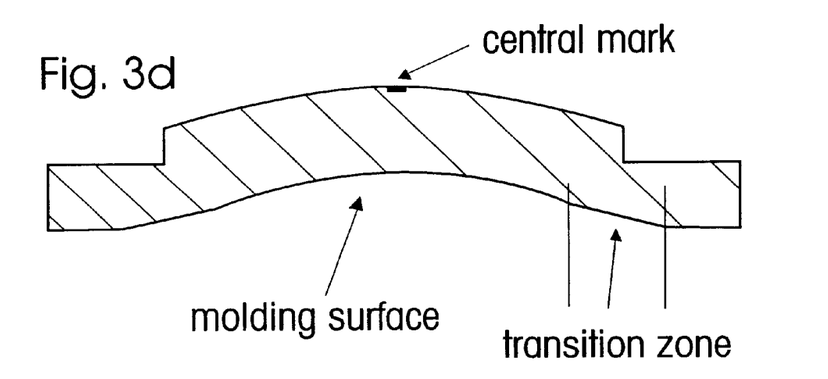

The application of a solution on the corneal surface prior to laser ablation promotes smoothing of the surface but it does not allow a major modification of the corneal shape in a large scale in respect to it's size in order to correct refractive errors such as myopia, hyperopia, regular and irregular astigmatism etc. Therefore, there is a need in the art for modulators that can be used in a single process to simultaneously correct the surface irregularities of the cornea and modify it's shape in a way that optimum optical performance is achieved (FIGS. 1, 2). It is the object of the disclosed invention to provide suitable materials, accurate methods and special devices for the preparation of centered photoablatable modulators on the corneal surface. These modulators have a posterior surface that contacts the cornea and follows it's shape filling all the irregularities, while their anterior surface has a predetermined position and shape in respect to the cornea to be treated.

A material found to be suitable for the preparation of modulators is a gelatin solution with the following properties:

It is prepared at temperatures 1 to 10 degrees below the boiling point of the solution and can be kept liquid at temperatures 50–55° C.

At a temperature of 40–45° C. it forms a rigid gel.

When solid it can be ablated with an ArF Excimer laser at fluences varying between 50 and 200 mJ/cm$^2$ (20 Hz repetition rate) without melting or deformation.

Under these conditions the ablation rate of the gel practically equals the ablation rate of the normal cornea.

The material can be prepared and stored in gel form at room temperatures in air tight containers.

It is fully thermoreversible and it can be heated above it's solution to gel transition point prior to use in order to form a homogeneous solution.

A mixture of porcine skin gelatin and vegetable gelatin (carrageenan) has been found to be suitable for the preparation of a solution with the above properties. Concentration of porcine skin gelatin can be varied from about 10% to about 25% and concentration of carrageenan can be from about 0.2% to about 5% w/w A small quantity of a dye (e.g. Sodium Fluorescein) can be added in the gelatin solution in order to produce a colored gel. A colored modulator has the advantage that it can be visually distinguished from the cornea and the ablation process can be terminated when the modulator is removed thoroughly.

Additionally, an anesthetic (e.g. tetracaine or proparacaine) added in the solution may render the molding an ablation process more comfortable for the patient.

A device suitable for the in-situ molding of the modulator comprises the following parts:

a) Lightweight mold constructed of transparent material having at least one molding surface which has optical quality and is being imprinted on the anterior surface of the gel and corresponds to the desired post-ablation shape of the cornea. In a preferred embodiment this mold has the shape of a hard contact lens with a peripheral transition zone to a flat area and a central mark. This mold remains on the surface of the gel until the gel completely solidifies (typically 3–5 min after application). After the lapse of this interval the mold is being removed. In a preferred embodiment the shape of the molding surface is spherical having a radius of curvature ranging from about 7 mm to about 10 mm. In another preferred embodiment the shape of the molding surface is ellipsoid having a base curvature from about 7 mm to 10 mm and an eccentricity ranging from about 0.1 to about 0.5.

b) Reference ring which attaches on an area of the eye outside the optical zone and serves as a guide which enables the precise placement of the mold in respect to the cornea. The plane defined from the circle of contact between the reference ring is perpendicular to the axis of symmetry of the mold. In a preferred embodiment this reference ring may attach in an area of the sclera. In another preferred embodiment it may be designed to fit a peripheral part of the cornea having a diameter from about 8 mm to about 10 mm. In another embodiment the reference ring may be designed to fit the limbus. In another embodiment the reference ring may feature a number of legs in order to ensure stable contact in the case of irregular shape of the eye. These legs may vary in length individually in order to control the orientation of the level of the reference ring in respect to the level defined by the points of contact. The reference ring may incorporate air suction for it's attachment on the eye. The reference ring guides either the mold itself or it's holder. In a preferred embodiment the reference ring is placed under the mold and serves as a base for the placement of the mold on top of it. In another preferred embodiment the mold is placed centrally on the cornea with arbitrary orientation and the reference ring is used to align the mold. (Reference ring: FIGS. 3a–3e)

c) Holder for the mold that works with the reference ring and assists the placement of the mold in the reference ring. This holder is designed in such a way that it allows the observation of the biggest part of the mold during it's placement. After the placement of the mold on the desired position the mold holder releases the mold in place without displacing or applying any stress capable of deforming it. In a preferred embodiment the holder of the mold is made of a transparent material and the mold is attached to it by means of air suction. In another preferred embodiment the holder is designed as forceps.

d) Diaphragm (iris) for the determination of the irradiation zone. In some cases the laser used for the ablation of the modulator and part of the cornea, may use an external variable diaphragm for the creation of the desired ablation profile (e.g. Aesculap Meditec lasers). For these cases, since the irradiation is uniform and the corneal ablation profile is created by the modulator, a stationary diaphragm must be used for the confinement of the laser radiation in the ablation zone. Additionally this diaphragm must be designed in such a way that allows it's use in conjunction with the reference ring. In a preferred embodiment the diaphragm has the shape of a washer that fits centered in the reference ring after the removal of the mold holder.

It is obvious that for the correct application of the procedure and the precise preparation of customized modulators, the use of a mold that fits the requirements of the cornea to be treated is necessary. In a preferred embodiment the mold is selected from a series of pre-existent molds.

After the gel solidification the mold is being removed to uncover an in situ molded modulator which removes the presumable geometrical irregularities of the cornea and additionally shapes the cornea in order to correct refractive errors of the eye.

The molding surface of the mold used to create a modulator for a given cornea is preferably selected so that a minimal quantity of gel is needed to fill the space between the corneal surface and the molding surface of the mold. For this purpose preoperative corneal topography or keratometry data can be utilized. In general, methods similar to these used for contact lens fitting can be used for mold selection.

In a preferred embodiment the molding surface is aspheric in order to minimize the spherical aberration of the postoperative shape of the cornea.

Given the desirable shape of the cornea after the treatment and the central depth of ablation (modulator central thickness+depth of ablation at corneal apex), it is possible to calculate the correct shape of the molding surface in order to compensate for the central flattening that occurs upon ablation of convex surfaces with homogeneous distribution of irradiation (Hyperopic shift).

The reference ring may remain in place after the preparation of the modulator for the stabilization of the eye during the irradiation process.

The holder of the mold or the mold itself may optionally have the necessary weight to assist application in case of solutions with high viscosity.

It is obvious that optical axis of the modulator (and consequently the optical axis of the cornea post-ablation) must coincide with the optical axis of the crystalline lens in order to have on ocular optical system with acceptable performance.

For the precise centering and alignment of the mold in respect to the optical axis of the rest of the eye, and particularly for the initial centering of the reference ring, optical elements such as light sources, lenses, mirrors, apertures and marks may be comprised in the molding device.

In a preferred embodiment a point source lies on the axis of symmetry of the molding device. The patient observes this point source through the mold. The mold is optically coupled to the patient's cornea by means of an appropriate liquid (e.g. methyl cellulose) in order to eliminate the significance of presumable irregularities of the anterior corneal surface in patient's line of sight and vision generally. With this method the patient self aligns the optical axis of the eye to be treated with the axis of symmetry of the mold. At this point the reference ring is adjusted on the eye in order to comprise the reference plane for the mold holder. After this step, modulator gel is applied on the corneal surface and the mold is being put back to the position which was verified to be correct prior to gel application.

Another optical approach for initial alignment of the reference ring is the following:

The vertex of the cornea is being marked with a surgical marker. The molding device is being placed on the surface of the eye to a position for which the properly marked center of the mold, the marked center of the cornea and the reflection image of a light source that lies on the surgeon's line of sight (e.g. microscope light) lie on the same axis while the patient is observing the light source. At this point the reference ring can be attached to the surface of the eye to comprise the reference plane for the mold holder placement.

The optical elements utilized to assist the alignment of the modulator can either be parts of the device (built-in the reference ring or holder of the mold) or can be inserted externally only during the alignment process.

In another preferred embodiment the method used for the centering of the device is based on the assumption that the anatomic symmetry of the limbus or peripheral cornea is adequately accurate to define a plane perpendicular to the whole eye axis of symmetry. In this method the device is being placed on the surface of the eye to a position that a peripheral part of the mold fits the corresponding peripheral part of the cornea.

It has been noticed that the plume formed by the ablation by-products over the ablation site after each laser pulse can affect the homogeneity of the next pulse. This phenomenon is more intense as the pulse repetition rate increases. For the prevention of this effect and for the most efficient use of the laser energy the ablation debris must be removed. In a preferred embodiment a set of nozzles connected to external devices (e.g. air pumps, gas bottles etc.) is built in the reference ring to produce a gas flow capable of removing the ablation by-products over the ablation site.

The temperature of the modulator gel at the moment of contact with the cornea (48–52° C.) has been proved by histological methods to be safe for the cornea. However, a light irritation can occur during the first few postoperative days. For the prevention of this side effect, only the central part of the cornea which will be partially ablated should be exposed to the gel. The peripheral cornea can be protected by means of subsidiary components of the molding device. In a preferred embodiment the peripheral cornea is protected by a ring which has an internal opening with diameter slightly wider than the optical zone and is being put on the surface of the cornea before gel application. This ring protects the peripheral part of the cornea from unnecessary contact with the gel and confines the gel to the central (optical) zone.

In another embodiment the protective component may have the form of a membrane which covers the cornea prior to gel application. This membrane must be flexible in order to follow the shape of the cornea without distorting it and additionally it must have the same ablation rate with the cornea. In this case the membrane can optionally be colored in order to assist the visual distinguishing between cornea and the membrane so that the ablation process can be terminated when both modulator and membrane are removed thoroughly. In a different embodiment the membrane need not be photoablatable. In this case it must feature a central opening which corresponds to the extend of the optical zone to be treated. In this case the membrane could serve also as the diaphragm for the confinement of laser radiation.

BRIEF DESCRIPTION OF THE DRAWINGS

FIG. 6 illustrates steps for the preparation of an centered modulator comprising the steps of:

6a. Adjustment of reference ring with mold in place.

6b. Application of an effective amount of hydrogel.

6c. Placement of mold centrally on the cornea.

6d. Reapplication of the pre-adjusted reference ring for the alignment of the mold.

EXAMPLE 1

Gel Preparation

A quantity of 1.6 g of porcine skin gelatin (Type A, bloom 300, available from SIGMA) and 0.0780 g vegetable gelatin (carrageenan Kappa type, available from SIGMA) are mixed in a dry glass pot. Nanopure water in a quantity of 6 ml is added. The mixture is being heated in a microwave oven to a temperature of 90 to 95° C. for about 20 minutes to form a homogeneous solution. After the complete dissolution of the gelatins, sodium fluorosceine aqueous solution 1% is added in a quantity of 0.5 ml. Sterile syringes of 1 ml capacity with air tight caps are being filled with 0.5 ml of the solution each. If no additional sterilization is applied after the syringes filling (e.g. gamma ray), the modulator material can be stored at room temperatures (gel form) inside the syringes for at least 3 months without noticeable change of it's physical properties.

EXAMPLE 2

Usage and Operation of Centration Device

A syringe containing 0.5 ml of the previously prepared gel is heated in a water bath to a temperature of about 90° C. for 10 minutes to liquefy the gel. The syringe with the liquefied gel is then inserted in a water bath having a temperature of 52° C. in order to cool down to a safe temperature for the cornea. A time interval of 10 minutes in the 52° C. water bath has been found to be adequate for the syringe—material—water bath system to reach thermal equilibrium. The reference ring of the molding device is centered with a process which comprises the steps of:

positioning of the reference ring on the surface of the eye to be treated insertion of the mold holder (with a mold attached) to the guide or slide way of the reference ring positioning of the reference ring in respect to the eye in such a way that the peripheral zone of the mold fits the corresponding peripheral zone of the cornea adjustment of the variable stop in order to minimize the mean distance of the molding surface from the cornea and thus ensure a minimal modulator thickness fixation of the eye by means of pressing the reference ring against the surface of the eye removal of mold holder while the position of reference ring in respect to the eye is maintained.

After the centering of the reference ring, a quantity of about 0.1 ml of the liquefied gel which is contained in the preheated syringe is applied on the central part of the cornea.

The holder of the mold is then reinserted in the guide and the mold is released in contact with the gel reinsertion of the mold holder to the guide or slide way of the reference ring, release of the mold in contact with the gel and removal of the mold holder.

After the lapse of the time interval needed for the solidification of the gel (4 minutes) the mold is being removed from gel surface.

The modulator remains on the corneal surface with an anterior surface smooth and centered in respect to the anatomical characteristics of the peripheral cornea.

EXAMPLE 3

Usage and Operation of Centration Device

A syringe containing 0.5 ml of the previously prepared gel is heated in a water bath to a temperature of about 90° C. for 10 minutes to liquefy the gel. The syringe with the liquefied gel is then inserted in a water bath having a temperature of 52° C. in order to cool down to a safe temperature for the cornea. A time interval of 10 minutes in the 52° C. water bath has been found to be adequate for the syringe—material—water bath system to reach thermal equilibrium.

The reference ring of the molding device is centered with a process which comprises the steps of:

- positioning of the reference ring on the surface of the eye to be treated
- insertion of the mold holder (with a mold attached) to the guide or slide way of the reference ring
- applying on the corneal surface of isotonic solution in order to optically couple the cornea and the mold
- insertion of the mold holder to the guide of the reference ring
- patient self-alignment of line of sight with axis of symmetry of said mold by means of patient observing a light source which is positioned on the axis of symmetry of mold.
- adjustment of the variable stop in order to minimize the mean distance of the molding surface from the cornea and thus ensure a minimal modulator thickness
- fixation of the eye by means of pressing the reference ring against the surface of the eye
- removal of mold holder while the position of reference ring in respect to the eye is maintained.

After the centering of the reference ring, the surface of the cornea is being cleaned (if necessary) and a quantity of about 0.1 ml of the liquefied gel which is contained in the preheated syringe is applied on the central part of the cornea.

The holder of the mold is then reinserted in the guide and the mold is released in contact with the gel.

After the lapse of the time interval needed for the solidification of the gel (4 minutes) the mold is being removed from gel surface.

The modulator remains on the corneal surface with an anterior surface smooth and centered in respect to the line of sight of the given eye.

EXAMPLE 4

Usage and Operation of Centration Device

A syringe containing 0.5 ml of the previously prepared gel is heated in a water bath to a temperature of about 90° C. for 10 minutes to liquefy the gel. The syringe with the liquefied gel is then inserted in a water bath having a temperature of 52° C. in order to cool down to a safe temperature for the cornea. A time interval of 10 minutes in the 52° C. water bath has been found to be adequate for the syringe—material—water bath system to reach thermal equilibrium.

The anatomical center of the cornea is being marked by means of a marker that fits the limbus and features a central marking pin.

Figure 4A:
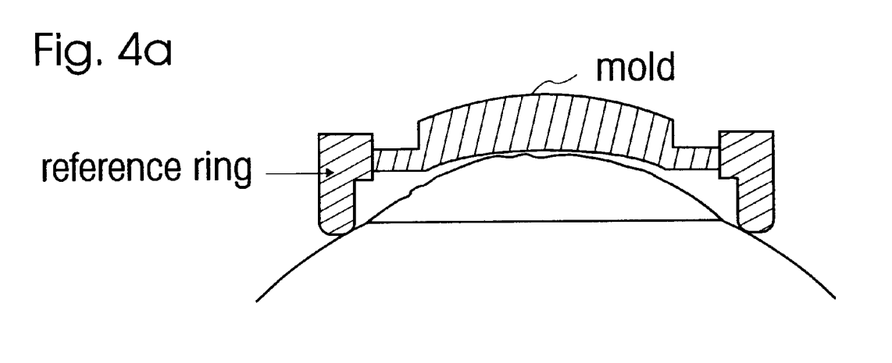
FIGS. 4a–4f illustrate possible configurations of the reference ring.
Figure 4B:
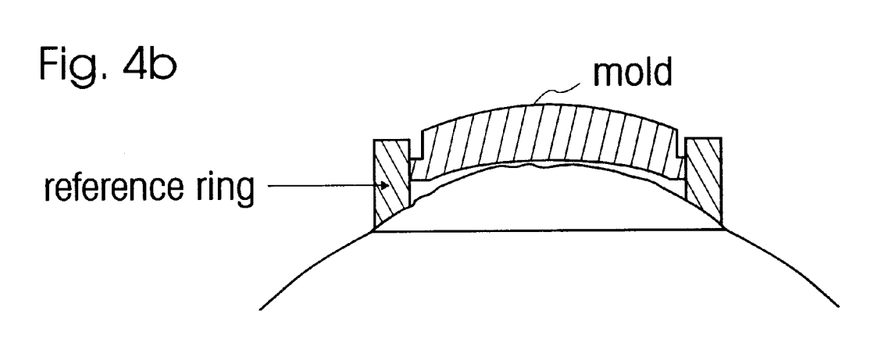
Figure 4C:
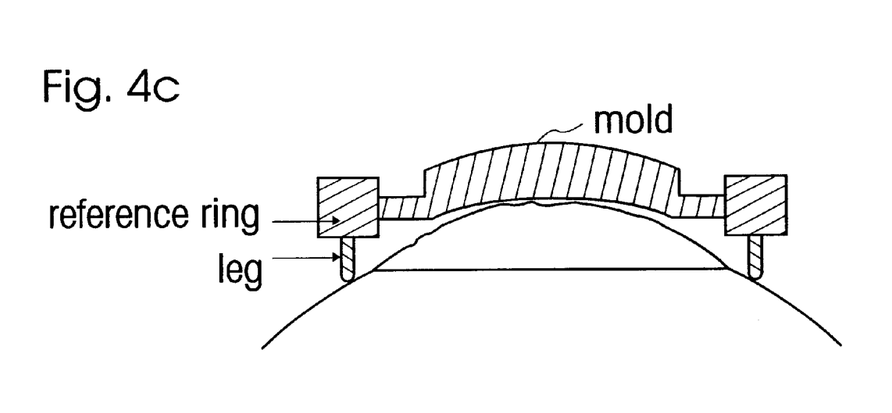
Figure 4D:
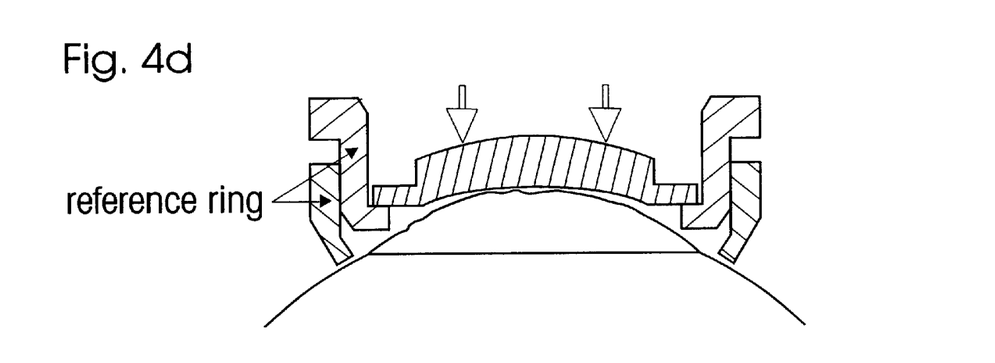
Figure 4E:
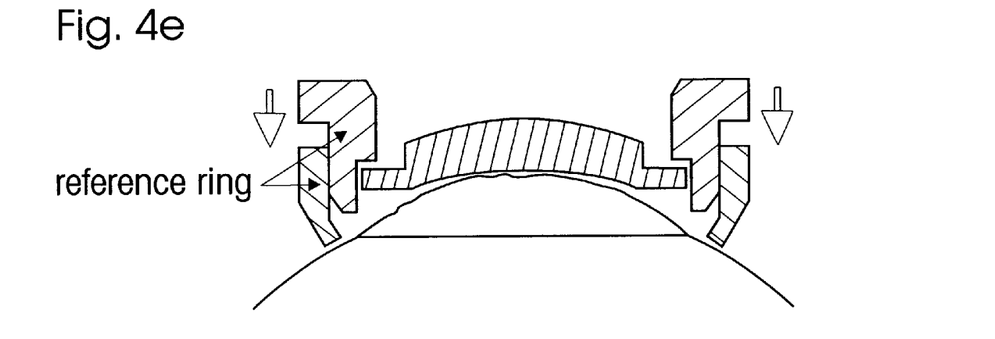
Figure 4F:
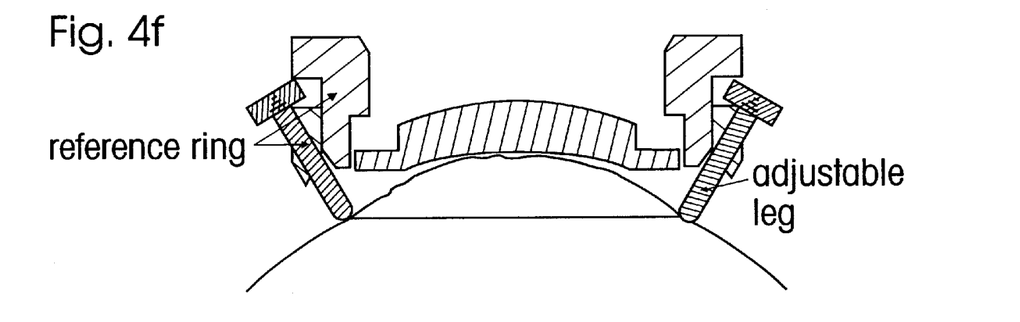
Figure 5:
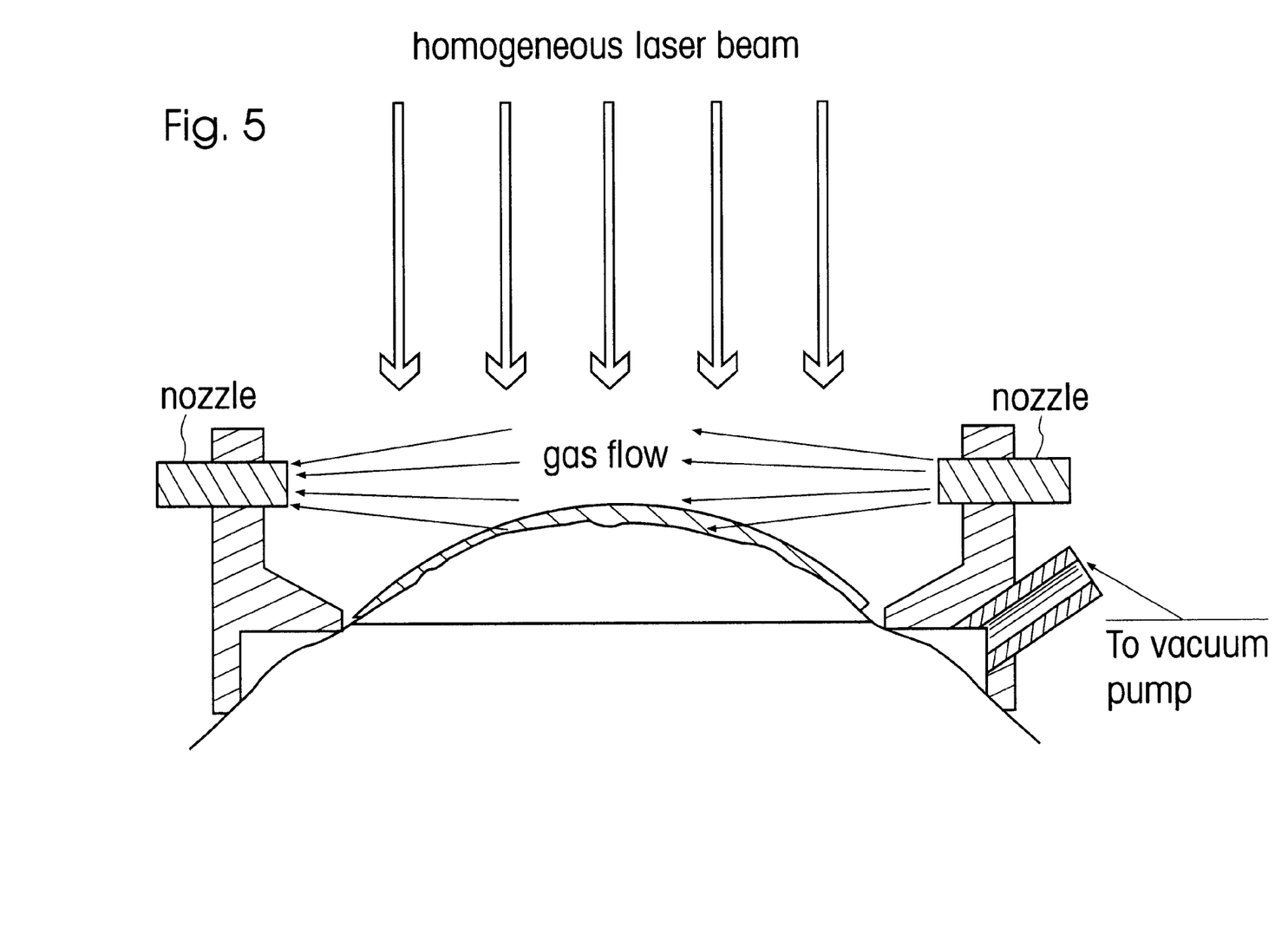
FIG. 5 illustrates a reference ring that can be used during photoablation which comprises a vacuum ring for it's attachment on the eye and gas flow nozzles for the removal of the ablation debris.
Figure 6A:
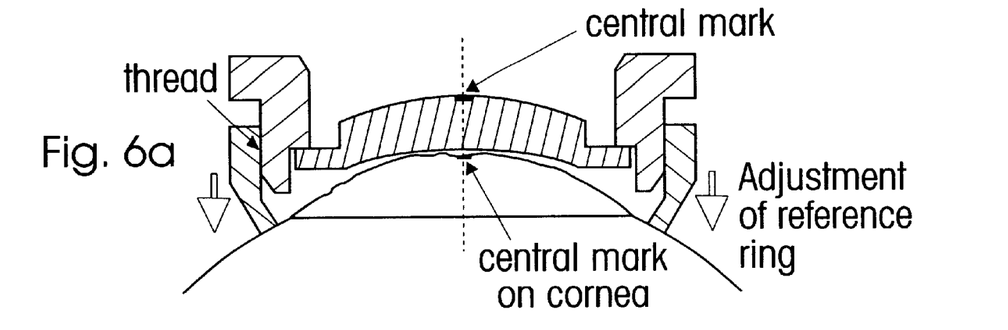
Figure 6B:
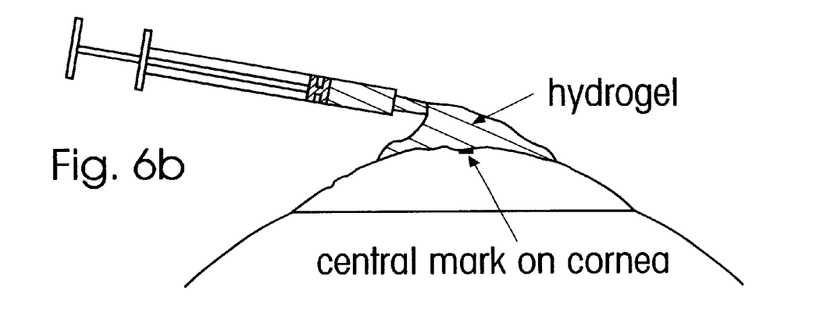
Figure 6C:
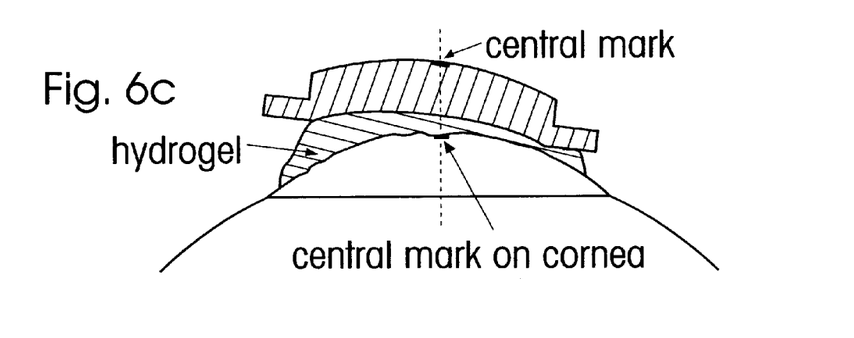
Figure 6D:
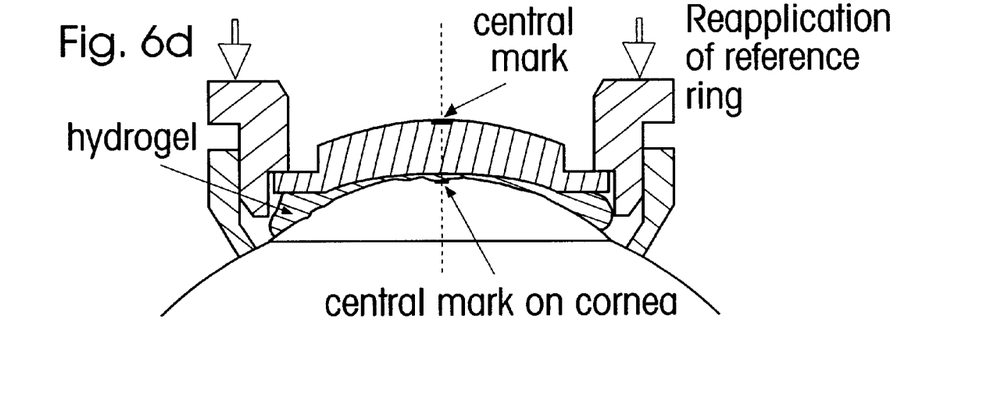

A mold featuring a central mark is being placed on the surface to be treated in a manner that the center of the mold lies over the anatomical center of the cornea. The reference ring having adjustable legs (see FIGS. 4e–4f) is being placed over the mold and adjusted in order to ensure that the optical axis of the mold is perpendicular o the plane defined by the limbus.

After the adjustment of the reference ring, the mold is being removed the surface of the cornea is being cleaned (if necessary) and a quantity of about 0.1 ml of the liquefied gel which is contained in the preheated syringe is applied on the central part of the cornea.

The mold is then repositioned centrally on the cornea and the (pre-adjusted) reference ring is utilized to align the mold. It is noticeable that this approach does not incorporate a specially designed mold holder.

After the lapse of the time interval needed for the solidification of the gel (4 minutes) the mold is being removed from gel surface.

The modulator remains on the corneal surface with an anterior surface smooth and centered in respect to the line of sight of the given eye.

EXAMPLE 5

Irradiation Process

After the preparation of the modulator, the surface of the gel is being irradiated with an ArF Excimer laser beam having an energy fluence of about 150 mJ/cm$^2$ and a repetition rate of about 20 Hz. The area of the modulator which corresponds to the optical zone is irradiated homogeneously. During the ablation process and due to the irregular shape of the cornea, different portions of the cornea will be exposed to laser radiation after different number of laser pulses. This will result in smoothening of the corneal surface as the more elevated parts will be subjected to more ablation than the less elevated.

The irradiation process is continued until all the modulator material is removed from the surface of the cornea. This condition is visually perceived by the termination of the fluorescein characteristic green fluorescence.

What is claimed is:

1. A hydrogel for the preparation of a laser beam modulator, characterized by the following properties:

is liquid at temperatures ranging from 50 degrees C. to 55 degrees C.;

at a temperature ranging from 40° C. to 45° C. forms a rigid gel having approximately the same ablation rate with the human cornea;

moldable in stable lenticular shapes prior to or during solidification;

adheres to the cornea;

fluoresces characteristically under excimer laser irradiation;

an aqueous solution of a mixture of Type A gelatin from porcine skin in concentration ranging between about 10% to about 25%, carrageenan kappa type in concentration ranging from about 0.2% to about 5% w/w and sodium fluorescein in concentration ranging between about 1 µgr/ml to about 5 µgr/ml.

2. A hydrogel for the preparation of a laser beam modulator, the hydrogel comprising:

an aqueous solution of a mixture of Type A gelatin from porcine skin in concentration ranging between about 10% to about 25%, carrageenan kappa type in concentration ranging from about 0.2% to about 5% w/w and sodium fluorescein in concentration ranging between about 1 µgr/ml to about 5 µgr/ml.

* * * * *